United States Patent
Van Der Kooi et al.

(10) Patent No.: US 10,433,755 B2
(45) Date of Patent: Oct. 8, 2019

(54) METHOD AND SYSTEM FOR DETERMINING A PARAMETER WHICH IS INDICATIVE FOR WHETHER A PATIENT IS DELIRIOUS

(71) Applicant: UMC UTRECHT HOLDING B.V., Utrecht (NL)

(72) Inventors: Arendina Wilhelmina Van Der Kooi, Utrecht (NL); Arjen Jacob Cornelis Slooter, Utrecht (NL)

(73) Assignee: PROLIRA B.V., Utrecht (NL)

( * ) Notice: Subject to any disclaimer, the term of this patent is extended or adjusted under 35 U.S.C. 154(b) by 334 days.

(21) Appl. No.: 15/023,074

(22) PCT Filed: Sep. 19, 2013

(86) PCT No.: PCT/EP2013/069521
§ 371 (c)(1),
(2) Date: Mar. 18, 2016

(87) PCT Pub. No.: WO2015/039689
PCT Pub. Date: Mar. 26, 2015

(65) Prior Publication Data
US 2016/0228028 A1    Aug. 11, 2016

(51) Int. Cl.
| | | |
|---|---|---|
| A61B 5/00 | (2006.01) |
| A61B 5/0476 | (2006.01) |
| A61B 5/0478 | (2006.01) |
| A61B 5/048 | (2006.01) |
| A61B 5/16 | (2006.01) |
| A61B 5/04 | (2006.01) |

(52) U.S. Cl.
CPC ............ *A61B 5/0478* (2013.01); *A61B 5/048* (2013.01); *A61B 5/04012* (2013.01);
(Continued)

(58) Field of Classification Search
USPC ......................................................... 600/544
See application file for complete search history.

(56) References Cited

U.S. PATENT DOCUMENTS

| | | |
|---|---|---|
| 5,230,346 A | 7/1993 | Leuchter |
| 6,021,246 A | 2/2000 | Koshiyama et al. |
| (Continued) | | |

OTHER PUBLICATIONS

Van der Kooi et al. Delirium Detection Using EEG: What and How to Measure. CHEST 2015; 147(1):94-101.*

(Continued)

*Primary Examiner* — Etsub D Berhanu
(74) *Attorney, Agent, or Firm* — Hudak, Shunk & Farine Co. LPA (57) ABSTRACT

Method for determining a parameter which is indicative for whether a patient is delirious or not, or is at risk of becoming delirious or not, wherein the method comprises the steps of: —providing electroencephalography (EEG) data comprising recording signals from at least two electrodes located on different locations on the patient's scalp during a predetermined time period, for instance at least 10 seconds, wherein at least one of the signals is recorded from the frontal half on the scalp; —processing said EEG data for obtaining a deviation signal from the two recording signals from the electrodes; —analyzing said deviation signal in the frequency spectrum for establishing slowing of said deviation signal and defining the parameter as the degree of slowing of said deviation signal which in combination with the locations of the recordings on the patient's scalp is indicative whether said patient is delirious or not, or is at risk of becoming delirious or not.

17 Claims, 4 Drawing Sheets

(52) U.S. Cl.
CPC ............ *A61B 5/0476* (2013.01); *A61B 5/165* (2013.01); *A61B 5/6814* (2013.01); *A61B 5/7257* (2013.01)

(56) References Cited

U.S. PATENT DOCUMENTS

| | | |
|---|---|---|
| 6,097,980 A | 8/2000 | Monastra et al. |
| 2007/0100251 A1* | 5/2007 | Prichep ............ A61B 5/04009 600/544 |

OTHER PUBLICATIONS

Moretti et al. Individual analysis of EEG frequency and band power in mild Alzheimer's disease. Clinical Neurophysiology 115 (2004) 299-308.*

Hogan et al. Memory-related EEG power and coherence reductions in mild Alzheimer's disease. International Journal of Psychophysiology 49 (2003) 147-163.*

Koponen et al. EEG spectral analysis in delirium. Journal of Neurology, Neurosurgery, and Psychiatry 1989;52:980-985.*

Jacobson et al. Conventional and quantitative EEG in the diagnosis of delirium among the elderly. Journal of Neurology, Neurosurgery, and Psychiatry 1993;56:153-158.*

Van der Kooi et al. What Are the Opportunities for EEG-Based Monitoring of Delirium in the ICU? The Journal of Neuropsychiatry and Clinical Neurosciences 2012; 24:472-477.*

Hier et al. Quantitative Measurement of Delta Activity in Alzheimer's Disease. Clinical Electroencephalography (1991) vol. 22, No. 3.*

Onoe, S., EEG spectral analysis in children with febrile delirium, Brain & Development Journal, 2004, pp. 513-518, vol. 26, Elsevier, Amsterdam, Netherlands, XP4632395A.

* cited by examiner

METHOD AND SYSTEM FOR DETERMINING A PARAMETER WHICH IS INDICATIVE FOR WHETHER A PATIENT IS DELIRIOUS

The present invention relates to a method and system for determining a parameter which is indicative for whether a patient is delirious or not or is at risk of becoming delirious or not.

Delirium is an acute disturbance of consciousness and cognition that usually fluctuates over time. It is a common disorder, with reported incidences of more than 60% during Intensive Care Unit (ICU) stay and over 15% on a geriatric ward or medium care unit. Delirium is associated with higher mortality, longer hospital stay, long-term cognitive impairment and increased costs. There are three different subtypes of delirium based on psychomotor behavior: hypoactive, hyperactive and mixed-type delirium.

Despite its frequency and impact, recognition of delirium by health care professionals is poor. Exceptions are hyperactive forms of delirium, but these are relatively rare. Furthermore, delayed treatment of delirium in ICU patients was found to increase mortality. In order to improve early diagnosis and treatment, the Society of Critical Care Medicine and the American Psychiatric Association recommend daily monitoring of delirium in ICU patients. Various delirium assessment tools have been developed. Of these, the Confusion Assessment Method for the ICU (CAM-ICU) had highest sensitivity in ICU patients. However, the sensitivity of the CAM-ICU in routine, daily practice appeared to be low (overall 47%), particularly to detect the hypoactive type of delirium (sensitivity 31%) and delirium in postoperative patients. Unfortunately, the CAM-ICU has more limitations. Firstly, it cannot quantify the severity of delirium and secondly, cognitive screening does not fit well in the culture of the ICU that is primarily orientated on monitoring of physiological alterations. These factors hinder early treatment and may therefore impair outcome. Moreover, research on delirium in the ICU is hampered by the lack of a sensitive tool for monitoring.

It is therefore a goal of the present invention, amongst other goals, to provide a reliable and efficient method for the determination of a parameter which is indicative for whether a patient is delirious or not.

This goal, amongst other goals, is met by a method according to appended claim 1. More specifically, this goal, amongst other goals, is met by a method for determining a parameter which is indicative for whether a patient is delirious or not or is at risk of becoming delirious, wherein the method comprises the steps of:

providing electroencephalography (EEG) data comprising recording signals from at least two electrodes located on different locations on the patient's scalp during a predetermined time period, for instance at least 10 seconds, wherein at least one of the signals is recorded on the front half of the scalp;

processing said EEG data for obtaining a deviation signal from the two recording signals from the electrodes;

analyzing said deviation signal in the frequency spectrum for establishing slowing of said deviation signal and defining the parameter as the degree of slowing of said deviation signal which in combination with the locations of the recordings on the patient's scalp is indicative whether said patient is delirious or not or is at risk of becoming delirious.

The invention is based on the recognition that also a reliable parameter which can assist a physician in establishing whether a patient is delirious or not can be determined using the recordings of a minimal number of electrodes, for instance 2, 3, 4 or 5 electrodes. Applying all electrodes according to (extended) 10-20 EEG system is not necessary according to the invention.

The EEG data contains recording signals of the at least two electrodes which were located on different locations on the scalp of the patient during recording. The at least two recording signals are representative of brain activity as measured at these locations. The signals represent the change over time of the measured voltages, typically in the range of 10 µV-100 µV, during the predetermined time period.

Contrary to the general assumption that frontal electrode locations are less suitable for establishing an indicative parameter, due to the negative influence of eye movements, particular good results were obtained when at least one the signals was recorded on the front half of the scalp.

More specifically, according to a preferred embodiment, at least one of the signals is recorded from the frontal, central or temporal region as defined by the extended 10-20 EEG system (Modified Combinatorial Nomenclature). Even more specifically, a signal is preferably recorded at or near at least one of the locations indicated with $F_{px}$, $F_x$, $AF_x$, $FC_x$, $C_x$ or $T_x$, x representing each of the available locations. Most preferred in terms of efficiency of placement and reliable results are however the frontal ($F_x$) locations.

In particular good results are obtained if, according to a further preferred embodiment, the EEG data also comprises recording signals recorded from the parietal or occipital region on the patient's scalp as defined by the extended 10-20 EEG system (Modified Combinatorial Nomenclature). According to this embodiment, at least one electrode is located on the front half of the scalp and at least one electrode is located on a parietal or occipital location. Specifically, a signal is preferably also recorded at or near at least one of the locations indicated with $TP_x$, $CP_x$, $P_x$, $PO_x$ or $O_z$, x representing each of the available locations.

More preferably, the EEG data comprises recording signals recorded from a location indicated with $F_8$, $F_{p2}$ or $F_{pz}$ and recording signals recorded from a location indicated with $P_z$, $P_3$, $O_1$ or $O_2$. According to a specific embodiment, as will be explained in more detail below, signals are recorded from only these two locations.

The signals obtained from these locations seem to provide a good basis for the determination of the parameter which can be efficiently used by a physician to establish whether the patient is delirious or not. In particular by calculating the relative delta power as parameter for these locations, as will be explained in greater detail below, a reliable parameter can be determined.

It should be noted that the invention is not limited to the exact locations as specified above. Some deviation from the locations is allowed, such that for instance also the positions on the scalp near, surrounding and between the mentioned locations are within the scope. A location is considered near a location specified according to the 10/20 system when such a location is between the specified location and an adjacent location as specified according to the 10/20 system. In fact, it is particularly advantageously that the exact placement of the electrodes according to the invention is less critical. Therefore, according to a further preferred embodiment, the EEG data comprises recording signals recorded from a location in the neighbourhood of the locations indicated with $F_8$, $F_{p2}$ or $F_{pz}$ and recording signals recorded from a location in the neighbourhood of the locations indicated with $P_z$, $P_3$, $O_1$ or $O_2$. A less critical placement of the electrodes increases the efficiency and usability of applying the electrodes to the patient.

The predetermined time period is preferably chosen such that a signal can be obtained which is representative of the brain activity while at rest. According to a preferred embodiment, the predetermined time period is in the range of 10 seconds-45 minutes, preferably approximately 1 minute.

The method, for instance during the step of processing, further preferably comprises selecting artifact free sections having a length of the predetermined time period from the EEG data. These signal sections are then used for obtaining the deviation signal. Artifacts, for instance caused by eye or head movement or blinking, are disturbances in the recorded EEG signal which influence the determination of the parameter. It is thus preferred that the EEG data, or at least the signals used as input for the processing step, contains signals being free from artifacts during the predetermined time period. The processing step then preferably comprises obtaining a deviation signal from the two artifact free recording signals. It may be preferable to obtain EEG data having a length of a longer predetermined time period to be able to select a length of artifact free signals having a length of the predetermined time period from this longer predetermined period.

In the processing step, the difference between the two signals is preferably calculated, for instance by subtracting the first signal from the second signal. By using a deviation of two recordings of brain waves, a reliable parameter can be determined. This deviation signal therefore represents the difference in measurements, in particular in terms of voltages, as measured between the two electrodes during the predetermined time period. Preferably the step of processing comprises obtaining at least one bipolar deviation from said two electrodes as the signal being representative of the difference between the measurements of the electrodes. It is remarked that although only a limited number, for instance two, of recordings from electrodes are used according to the invention, it may be possible that for instance an additional electrode is used as a ground electrode for obtaining the signals of the two other electrodes.

The thus obtained deviation signal which preferably corresponds to the difference in measurement signals of the two electrodes is then analyzed to determine the parameter which is indicative whether the patient is delirious or not. According to a specific embodiment, the invention relates to a non-diagnostic method for determining a parameter which is indicative whether a patient is delirious or not which can be used by a physician or other user to diagnose whether the patient is delirious or not or is at risk of becoming delirious, also taking into account other parameters and observations.

The invention is in particular directed towards determining a parameter which is indicative whether an awake, i.e. not sleeping and non-comatose, and non-sedated patient is delirious or not or is at risk of becoming delirious. The EEG data thereto preferably contains signals recorded while the patient was awake and non sedated. An even more reliable parameter can be determined when the EEG data contains signals recorded from the patient with eyes closed.

The parameter can not only be used as an indication for the physician whether the patient is delirious or not at the moment of recording, but is also usable in indicating whether a patient is at risk of becoming delirious. It is for instance possible to determine the parameter according to the invention at different moments to indicate a trend. It may for instance be possible that the parameter at a given moment is not yet indicative of a delirium, but that a trend is visible towards a value of the parameter which is indicative of a delirium.

As said, the slowing of this deviation signal appears to be a good indication whether the patient is delirious or not. With the term slowing of the signal is meant a decrease in overall or relative frequency or a decrease or increase in a specific frequency band. The manner of calculating the degree of slowing and the locations of the electrodes from which the recording signals in EEG data are obtained, are chosen such that this parameter is indeed indicative for whether the patient is delirious or not.

In general terms, it is possible to establish a parameter as the relative power of a narrow frequency band, for instance in the order of magnitude having a width of 2-15 Hz, with respect to a broader frequency band, for instance 0.5-30 Hz. An increase in relative power of a frequency band in the lower range of the broader range is then indicative for slowing of the EEG. On the other hand, also a decrease in relative power of a narrower frequency band in the higher range, i.e. having higher frequencies, is indicative of slowing of the EEG and can therefore be used as a parameter according to the invention.

More specifically, according to a preferred embodiment, the step of analyzing comprises calculating the degree of slowing as the relative power of the deviation signal in at least one of the delta band (up to 4 Hz), the theta band (4-8 Hz), the alpha band (8-13 Hz) and the beta band (13-30 Hz) or a combination thereof. The relative power of a particular band is defined as the ratio between the power of the signal in said frequency band divided by the total power of each of the brain waves, preferably after filtering as will be explained in more detail below.

It should be noted that the invention is not limited to the exact ranges as indicated above, such that the deviations with respect to the upper and lower limits are within the scope.

A power spectrum of the deviation signal obtained from the step of processing is hereto calculated, for instance by a Fourier Transformation as known in the art. As an example, the power spectrum of the deviation signal is calculated using a Welch's averaged modified periodogram method of spectral estimation,
   using 8/(sample frequency) as segment length;
   using segments with 50% overlap;
   wherein any remaining entries that cannot be included in the segments of equal lengths are discarded;
   wherein each segment is windowed with a Hamming window that is the same length as the segment.

The power in the frequency band of each of the brainwaves, preferably 0.5-30 Hz after filtering as will be explained below, is summed as the absolute total power and the power in the relevant frequency band, for instance 0.5-4 Hz for the relative delta power, is then summed as the absolute power. The relative power is then defined by dividing the absolute power by the absolute total power. This relative power can then be used, provided that the locations of electrodes are suitable, as the parameter which is indicative whether a patient is delirious or not or is at risk of becoming delirious.

Using the relative power of the deviation signal in the delta band, the alpha band or the beta band as the parameter is preferred in view of the predicting capabilities. In particular reliable parameters were however obtained if the parameter is defined as the relative power of the deviation signal in the delta band (up to 4 Hz). Tests have concluded that the relative power in the delta band as the parameter allow a physician or another user to reliably predict whether the patient is delirious or not.

Another reliable determination is achieved if the parameter is defined as a ratio between the relative power of a lower frequency band, for instance in de delta or theta band, and the relative power of a higher frequency band, for instance in the alpha or beta band. More preferably the parameter is defined as the slow-fast ratio which is defined as:

(relative delta power+relative theta power)/(relative alpha power+relative beta power).

When, according to a different embodiment, the parameter is defined as the peak frequency, also reliable results have been obtained. The peak frequency is defined by the frequency with the maximal power in the frequency spectrum. A decrease of this peak frequency may be interpreted by a physician or other user that the patient is suffering from a delirium.

It is possible that the method simply returns the calculated parameter, for instance by displaying the resulting parameter on a screen, or by outputting a signal representative of the said parameter using a suitable output, for instance in the form of a connector.

It is however also possible that this parameter is compared to a predetermined threshold to provide the physician with extra information. If the calculated parameter meets the criterion, this can be interpreted by the physician as slowing of the relevant signal such that the patient may be delirious. Thresholds are dependent on the locations of the electrodes and the intended use in terms of specificity and sensitivity. As an example, the thresholds for the different parameters on for electrodes C4-O1 were found to be as listed in table 1:

TABLE 1

| Par | P-value | AUC | Sens (%) | Spec (%) | Thres | Crit |
|---|---|---|---|---|---|---|
| Delta | 2.48E−09 | 0.94 | 92 | 92 | 0.3753 | > |
| Alpha | 5.06E−09 | 0.93 | 85 | 88 | 0.1435 | < |
| S/F | 5.65E−08 | 0.91 | 92 | 81 | 2.9172 | > |
| Peak | 2.98E−06 | 0.86 | 81 | 1 | 6.3750 | < |
| Beta | 3.32E−05 | 0.82 | 84 | 76 | 0.0714 | < |
| Theta | 0.92 | 0.51 | 56 | 54 | 0.3444 | < |

With:
Par  Parameter:  Delta: relative delta power
                 Alpha: relative delta power
                 S/F:   slow-fast ratio
                 Peak:  peak frequency
                 Beta:  relative beta power
                 Theta: relative theta power
AUC  Area Under Curve of the receiver operating characteristic (ROC)
Sens Sensitivity
Spec Specificity
Thres Threshold
Crit Criterion: indication of delirium if test value is greater (>) or smaller (<) than threshold According to further preferred embodiment, the step of processing comprises filtering said EEG data for filtering out data having a frequency below a predetermined lower threshold and data having a frequency above a predetermined higher threshold, wherein the lower threshold is chosen between 0.1 Hz to 1 Hz, preferably 0.5 Hz, and wherein the higher threshold is chosen between 10 to 70 Hz, preferably 30 Hz. Preferably, the step comprises using a band pass FIR filter with cut-off frequencies of 0.5 and 30 Hz.

Figure 1:
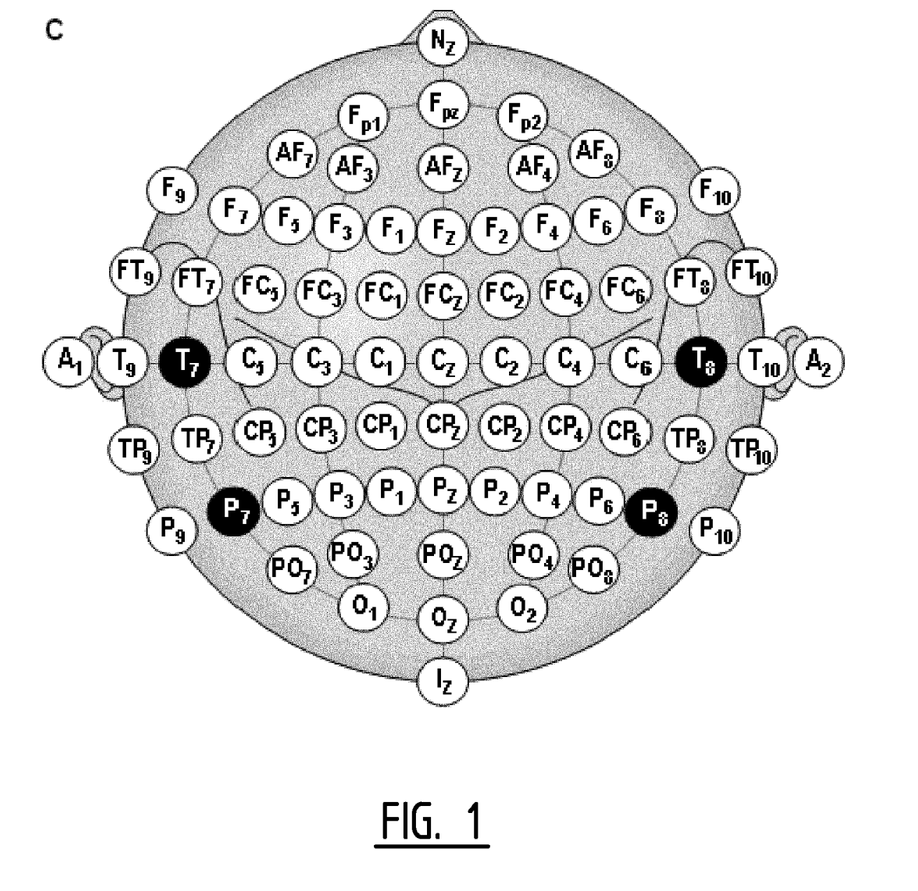
FIG. 1 shows the locations of the different electrodes in the extended 10/20 system.
Figure 2:
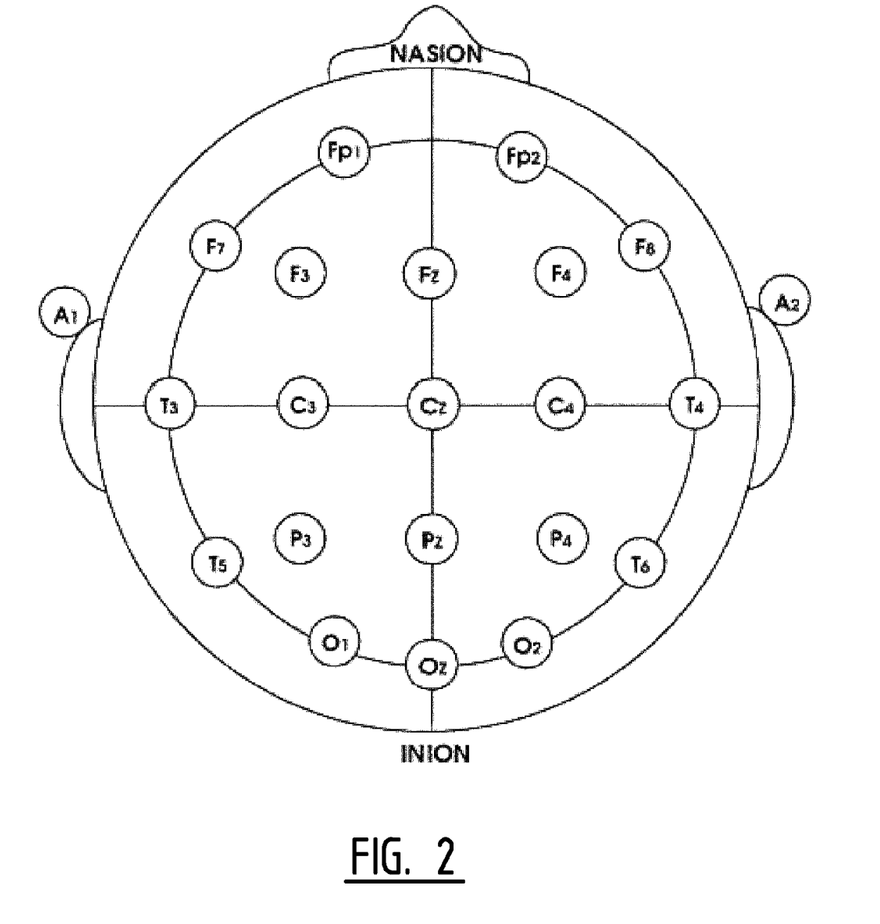
FIG. 2 shows the locations of the electrodes according to the classic 10/20 system.
Figure 3:
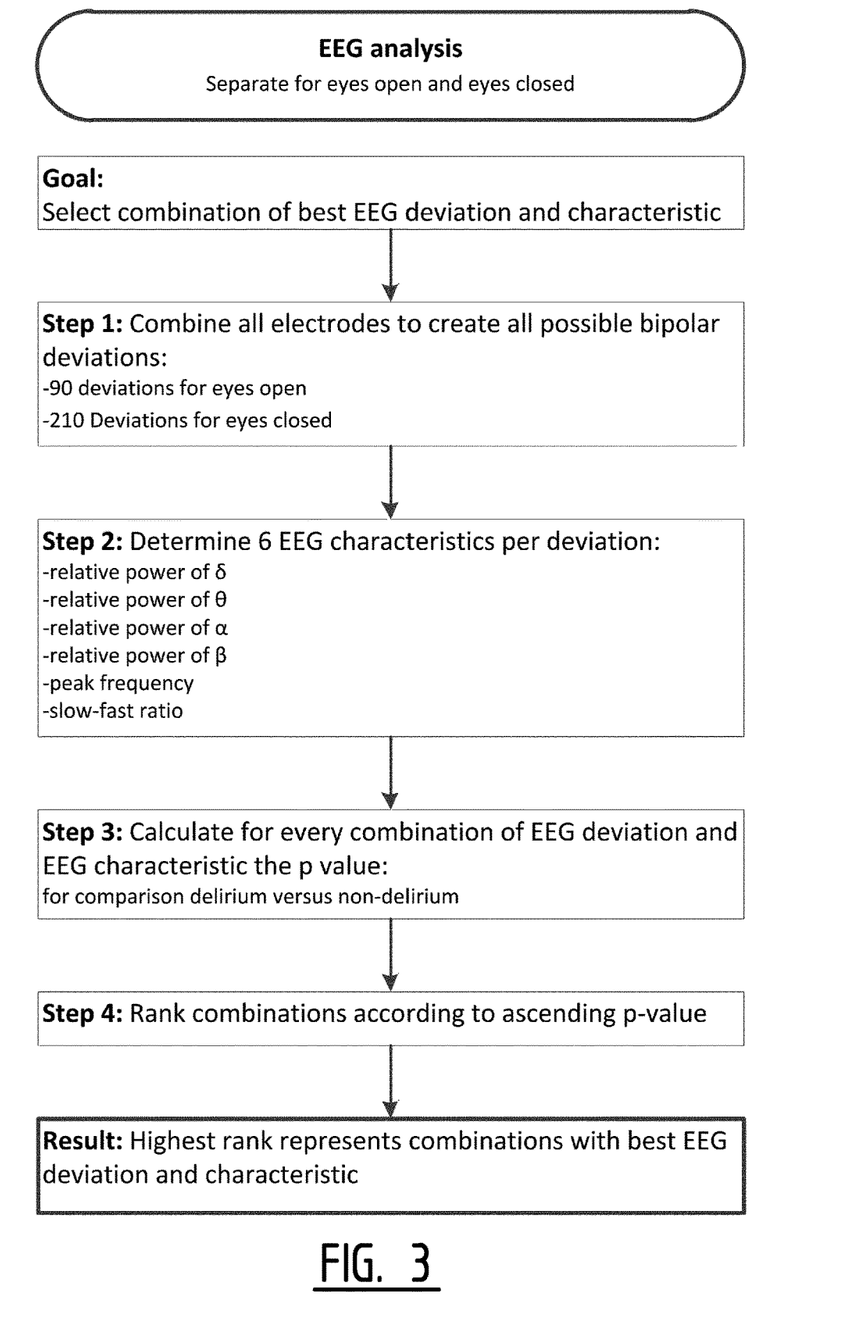
FIG. 3 shows a flow chart for the determination of combinations of locations and parameters for providing a indicative parameter according to the invention.

A particular advantage of the method of the invention is that only the recordings of limited number of electrodes, or even a single pair of electrodes, can be used to determine the parameter. According to a preferred embodiment, the parameter is based exclusively on the recordings of the limited number of electrodes, most preferably only two electrodes. It is therefore no longer necessary to include the recordings of all of the electrodes as prescribed by for instance the 10/20 system, see FIGS. 1 and 2. The EEG data therefore preferably contains recording signals of two electrodes only, which allows efficient processing due to a decrease in recordings compared to EEG recordings as known in the art.

More preferably, the EEG data is recorded only from the limited number of electrodes, for instance 2, 3, 4 or 5 and most preferably only 2. An extra, for instance third, electrode may however optionally be used a ground electrode during recording for establishing the signals being representative of the brain activity as measured at the two electrodes. Being able to determine a parameter which is indicative whether a patient is delirious or not using only this limited number of electrodes makes the method in particularly suitable for a routine clinical setting, for example the ICU. Although it is also possible to provide an indicative parameter using the deviations from each of the electrodes of the 10/20 system, such a system is too complicated to be practical in an ICU setting. Applying the minimal number of electrodes according to the invention is however not difficult and fits within the work process of clinical personnel.

As already mentioned, the parameter representative of the degree of slowing of the signal and the locations of the electrodes on the scalp of the patient must be chosen such that the resulting parameter is indeed indicative for whether the patient is delirious or not.

The determination of the positions of the two electrodes and the parameter to be calculated from the signals can be established by statistically comparing the different parameters being representative of the slowing of the signal obtained from each possible electrode pair deviation of the (extended) 10/20 system on a patient diagnosed to be delirious or not. This is preferably applied to a larger group of patients. Reference is made to the Example for determining combinations of locations and parameter as included below.

Table 2 as included below lists the results of this determination. It is noted that each of the electrode combinations as listed contains at least one electrode being positioned on the front half of the scalp according to the invention. According to a preferred embodiment, the EEG data contains recording signals obtained from locations on the scalp as listed in any of the rows of Table 2 as included below, wherein the column 'Loc 1' specifies the location of a first electrode in the extended 10/20 system, the column 'Loc 2' specifies the location of the second electrode in the extended 10/20 system, wherein the parameters marked with 'x' for the combinations of locations are indicative whether an awake, non-comatose patient with eyes closed is delirious or not, wherein:

Rel Alpha, Beta, Theta or Delta corresponds to the Relative Alpha, Beta, Theta or Delta Power as defined above, respectively;

S/F Ratio corresponds to the Slow-Fast Ratio as defined above;

Peak freq corresponds to the peak frequency as defined above.

TABLE 2

| Loc 1 | Loc 2 | Rel Alpha | Rel Beta | Rel Delta | S/F Ratio | Peak Freq |
|---|---|---|---|---|---|---|
| 'C3' | 'O1' | x | | x | x | |
| 'C3' | 'O2' | x | | x | x | x |
| 'C3' | 'P3' | x | | x | x | x |
| 'C3' | 'P4' | x | | x | x | x |
| 'C3' | 'P7' | x | | x | x | |
| 'C3' | 'P8' | x | x | x | x | x |
| 'C3' | 'Pz' | x | | x | x | x |
| 'C3' | 'T7' | x | | x | x | |
| 'C4' | 'C3' | x | x | x | x | |
| 'C4' | 'Cz' | x | x | x | x | |
| 'C4' | 'O1' | x | | x | x | x |
| 'C4' | 'O2' | x | x | x | x | x |
| 'C4' | 'P3' | x | | x | x | x |
| 'C4' | 'P4' | x | x | x | x | |
| 'C4' | 'P7' | x | x | x | x | x |
| 'C4' | 'P8' | x | x | x | x | |
| 'C4' | 'Pz' | x | x | x | x | x |
| 'C4' | 'T7' | x | x | x | x | |
| 'Cz' | 'C3' | x | x | x | x | |
| 'Cz' | 'O1' | x | x | x | x | |
| 'Cz' | 'O2' | x | x | x | x | x |
| 'Cz' | 'P3' | x | x | x | x | |
| 'Cz' | 'P4' | x | x | x | x | x |
| 'Cz' | 'P7' | x | x | x | x | |
| 'Cz' | 'P8' | x | x | x | x | x |
| 'Cz' | 'Pz' | x | x | x | x | |
| 'Cz' | 'T7' | x | x | x | x | |
| 'F10' | 'C3' | x | x | x | x | |
| 'F10' | 'C4' | x | x | x | x | |
| 'F10' | 'Cz' | x | x | x | x | |
| 'F10' | 'F3' | x | x | x | x | |
| 'F10' | 'F4' | x | x | x | x | |
| 'F10' | 'F7' | x | x | x | x | |
| 'F10' | 'Fp1' | x | | | x | |
| 'F10' | 'Fp2' | x | | | | |
| 'F10' | 'Fz' | x | x | x | x | |
| 'F10' | 'O1' | x | x | x | x | |
| 'F10' | 'O2' | x | x | x | x | |
| 'F10' | 'P3' | x | x | x | x | |
| 'F10' | 'P4' | x | x | x | x | |
| 'F10' | 'P7' | x | x | x | x | |
| 'F10' | 'P8' | x | x | x | x | |
| 'F10' | 'Pz' | x | x | x | x | |
| 'F10' | 'T7' | x | x | x | x | |
| 'F10' | 'T8' | x | x | x | x | |
| 'F3' | 'C3' | x | | x | x | |
| 'F3' | 'C4' | x | x | x | x | |
| 'F3' | 'Cz' | x | x | x | x | |
| 'F3' | 'F7' | x | | x | x | |
| 'F3' | 'O1' | x | | x | x | |
| 'F3' | 'O2' | x | | x | x | |
| 'F3' | 'P3' | x | | x | x | |
| 'F3' | 'P4' | x | | x | x | |
| 'F3' | 'P7' | x | | x | x | |
| 'F3' | 'P8' | x | | x | x | |
| 'F3' | 'Pz' | x | | x | x | |
| 'F3' | 'T7' | x | | x | x | |
| 'F3' | 'T8' | x | x | x | x | |
| 'F4' | 'C3' | x | x | x | x | |
| 'F4' | 'C4' | x | | x | x | |
| 'F4' | 'Cz' | x | x | x | x | |
| 'F4' | 'F3' | x | | x | x | |
| 'F4' | 'F7' | x | x | x | x | |
| 'F4' | 'Fz' | x | | x | x | |
| 'F4' | 'O1' | x | | x | x | |
| 'F4' | 'O2' | x | x | x | x | |
| 'F4' | 'P3' | x | x | x | x | |
| 'F4' | 'P4' | x | | x | x | |
| 'F4' | 'P7' | x | | x | x | |
| 'F4' | 'P8' | x | | x | x | |
| 'F4' | 'Pz' | x | | x | x | |
| 'F4' | 'T7' | x | | x | x | |
| 'F4' | 'T8' | x | x | x | x | |
| 'F7' | 'C3' | x | | x | x | |
| 'F7' | 'C4' | x | x | x | x | |
| 'F7' | 'Cz' | x | x | x | x | |
| 'F7' | 'O1' | x | | x | x | |
| 'F7' | 'O2' | x | x | x | x | |
| 'F7' | 'P3' | x | x | x | x | |
| 'F7' | 'P4' | x | x | x | x | |
| 'F7' | 'P7' | x | x | x | x | |
| 'F7' | 'P8' | x | x | x | x | |
| 'F7' | 'Pz' | x | x | x | x | |
| 'F7' | 'T7' | x | x | x | x | |
| 'F7' | 'T8' | x | x | x | x | |
| 'F8' | 'C3' | x | x | x | x | |
| 'F8' | 'C4' | x | x | x | x | |
| 'F8' | 'Cz' | x | x | x | x | |
| 'F8' | 'F3' | x | x | x | x | |
| 'F8' | 'F4' | x | | x | x | |
| 'F8' | 'F7' | x | x | x | x | |
| 'F8' | 'Fz' | x | x | x | x | |
| 'F8' | 'O1' | x | x | x | x | |
| 'F8' | 'O2' | x | x | x | x | |
| 'F8' | 'P3' | x | x | x | x | |
| 'F8' | 'P4' | x | x | x | x | |
| 'F8' | 'P7' | x | x | x | x | |
| 'F8' | 'P8' | x | x | x | x | |
| 'F8' | 'Pz' | x | x | x | x | x |
| 'F8' | 'T7' | x | x | x | x | |
| 'F8' | 'T8' | x | | x | x | |
| 'F9' | 'C3' | x | x | x | x | |
| 'F9' | 'C4' | x | x | x | x | |
| 'F9' | 'Cz' | x | x | x | x | |
| 'F9' | 'F10' | x | x | | x | |
| 'F9' | 'F3' | x | x | x | x | |
| 'F9' | 'F4' | x | x | x | x | |
| 'F9' | 'F7' | | x | x | x | |
| 'F9' | 'F8' | x | x | x | x | |
| 'F9' | 'Fp1' | x | | | x | |
| 'F9' | 'Fp2' | x | | x | x | |
| 'F9' | 'Fz' | x | x | x | x | |
| 'F9' | 'O1' | x | x | x | x | |
| 'F9' | 'O2' | x | x | x | x | |
| 'F9' | 'P3' | x | x | x | x | |
| 'F9' | 'P4' | x | x | x | x | |
| 'F9' | 'P7' | x | x | x | x | |
| 'F9' | 'P8' | x | x | x | x | |
| 'F9' | 'Pz' | x | x | x | x | |
| 'F9' | 'T7' | x | | x | x | |
| 'F9' | 'T8' | x | x | x | x | |
| 'Fp1' | 'C3' | x | | x | x | |
| 'Fp1' | 'C4' | x | x | x | x | |
| 'Fp1' | 'Cz' | x | x | x | x | |
| 'Fp1' | 'F4' | x | | | x | |
| 'Fp1' | 'F7' | x | | | | |
| 'Fp1' | 'F8' | x | x | x | x | |
| 'Fp1' | 'Fz' | x | | | | |
| 'Fp1' | 'O1' | x | | x | x | |
| 'Fp1' | 'O2' | x | x | x | x | |
| 'Fp1' | 'P3' | x | | x | x | |
| 'Fp1' | 'P4' | x | x | x | x | |
| 'Fp1' | 'P7' | x | | x | x | |
| 'Fp1' | 'P8' | x | x | x | x | |
| 'Fp1' | 'Pz' | x | x | x | x | |
| 'Fp1' | 'T7' | x | | x | x | |
| 'Fp1' | 'T8' | x | x | x | x | |
| 'Fp2' | 'C3' | x | x | x | x | |
| 'Fp2' | 'C4' | x | x | x | x | |
| 'Fp2' | 'Cz' | x | x | x | x | |
| 'Fp2' | 'F3' | x | | x | x | |
| 'Fp2' | 'F4' | x | | | | |
| 'Fp2' | 'F7' | x | x | x | x | |
| 'Fp2' | 'F8' | x | | | x | |
| 'Fp2' | 'Fp1' | x | | x | x | |
| 'Fp2' | 'Fz' | x | | x | x | |
| 'Fp2' | 'O1' | x | | x | x | |
| 'Fp2' | 'O2' | x | x | x | x | |
| 'Fp2' | 'P3' | x | | x | x | |
| 'Fp2' | 'P4' | x | | x | x | |
| 'Fp2' | 'P7' | x | | x | x | |
| 'Fp2' | 'P8' | x | | x | x | |
| 'Fp2' | 'Pz' | x | | x | x | |
| 'Fp2' | 'T7' | x | x | x | x | |

TABLE 2-continued

| Loc 1 | Loc 2 | Rel Alpha | Rel Beta | Rel Delta | S/F Ratio | Peak Freq |
|---|---|---|---|---|---|---|
| 'Fp2' | 'T8' | x | x | x | x | |
| 'Fz' | 'C3' | x | x | x | x | |
| 'Fz' | 'C4' | x | x | x | x | |
| 'Fz' | 'Cz' | x | x | x | x | |
| 'Fz' | 'F3' | x | x | x | x | |
| 'Fz' | 'F7' | x | x | x | x | |
| 'Fz' | 'O1' | x | x | x | x | |
| 'Fz' | 'O2' | x | x | x | x | x |
| 'Fz' | 'P3' | x | x | x | x | |
| 'Fz' | 'P4' | x | x | x | x | |
| 'Fz' | 'P7' | x | x | x | x | |
| 'Fz' | 'P8' | x | x | x | x | x |
| 'Fz' | 'Pz' | x | x | x | x | |
| 'Fz' | 'T7' | x | x | x | x | |
| 'Fz' | 'T8' | x | x | x | x | |
| 'T7' | 'O1' | x | | x | x | |
| 'T7' | 'O2' | x | | x | x | |
| 'T7' | 'P3' | x | | x | x | |
| 'T7' | 'P4' | x | x | x | x | |
| 'T7' | 'P7' | x | | x | x | |
| 'T7' | 'P8' | x | | x | x | x |
| 'T7' | 'Pz' | x | x | x | x | |
| 'T8' | 'C3' | x | x | x | x | |
| 'T8' | 'C4' | x | x | x | x | |
| 'T8' | 'Cz' | x | x | x | x | |
| 'T8' | 'O1' | x | x | x | x | |
| 'T8' | 'O2' | x | x | x | x | |
| 'T8' | 'P3' | x | x | x | x | |
| 'T8' | 'P4' | x | | x | x | |
| 'T8' | 'P7' | x | x | x | x | |
| 'T8' | 'P8' | x | | x | x | |
| 'T8' | 'Pz' | x | x | x | x | |
| 'T8' | 'T7' | x | x | x | x | |

The EEG data can be recorded beforehand to be subsequently processed and analyzed according to the invention. The data can thereto for instance be stored on a suitable information carrier. The step of providing the EEG data may therefore comprise loading the dataset in a suitable memory for further processing as is as such known in the art.

It is however also possible that the data is obtained by recording the signals from the two electrodes, preferably from only two electrodes, on the patient's scalp, for instance in (semi) real time.

The invention further relates to a system for determining a parameter which is indicative for whether a patient is delirious or not or is at risk of becoming delirious according to the method according to the invention, wherein the system comprises:

input means for receiving electroencephalography (EEG) data comprising recording signals from at least two electrodes located on different locations on the patient's scalp during a predetermined time period, for instance at least 10 seconds, wherein at least one of the signals is recorded from the front half of the scalp;

processing means for processing said EEG data for obtaining a deviation signal from the two recording signals from the electrodes;

analyzing means for analyzing said deviation signal in the frequency spectrum for establishing slowing of said deviation signal and for defining the parameter as the degree of slowing of said deviation signal which in combination with the locations of the recordings on the patient's scalp is indicative whether said patient is delirious or not or is at risk of becoming delirious;

output means for outputting said parameter.

The input means may for instance be formed by a suitable data carrier for receiving the EEG data previously obtained by recording the signals from the patient's scalp. The system according to the invention may for instance comprise a Personal Computer including a processor, memory and storage means as known in the art as such. It is however preferred if the system comprises a hand held, or at least portable, device provided with the input means, the processing, analyzing means and output means such that the device can be efficiently used in a routine clinical setting, for example the ICU.

The analyzing means and processing means may be formed integrally and may for instance be formed, or comprise, a suitable processor arranged for processing data as known in art as such.

The input means may further comprise a suitable connector, or a plurality thereof, arranged for connecting the electrodes for recording the signals from the patient's scalp, preferably only two electrodes and possibly a third ground electrode according to the invention.

As said, according to the invention, a reliable parameter can be established by using the signals as recorded from two electrodes on the patient's scalp. Therefore, according to a further preferred embodiment, the input means comprise at least two electrodes arranged to be placed on different locations on the patient's scalp for obtaining the two recording signals.

According to a preferred embodiment of a system which is especially efficient for use in routine clinical setting such as the ICU, the input means comprise only two electrodes arranged to be placed on different locations on the patient's scalp for obtaining the two recording signals. A system using only two electrodes, and possibly a third ground electrode, has a compact structure which can be efficiently used in a routine clinical setting as explained above.

According to a further preferred embodiment, the output means comprise a display for displaying a representative of the parameter. The display may for instance display the calculated parameter, such as the relative delta power as explained above. This parameter can then be taken into account by the physician or other user of the system for determining whether the patient is delirious or not.

The present invention is further illustrated by the following examples according to preferred embodiments of the method according to the invention, and are not intended to limit the scope of the invention in any way.

Figure 4:
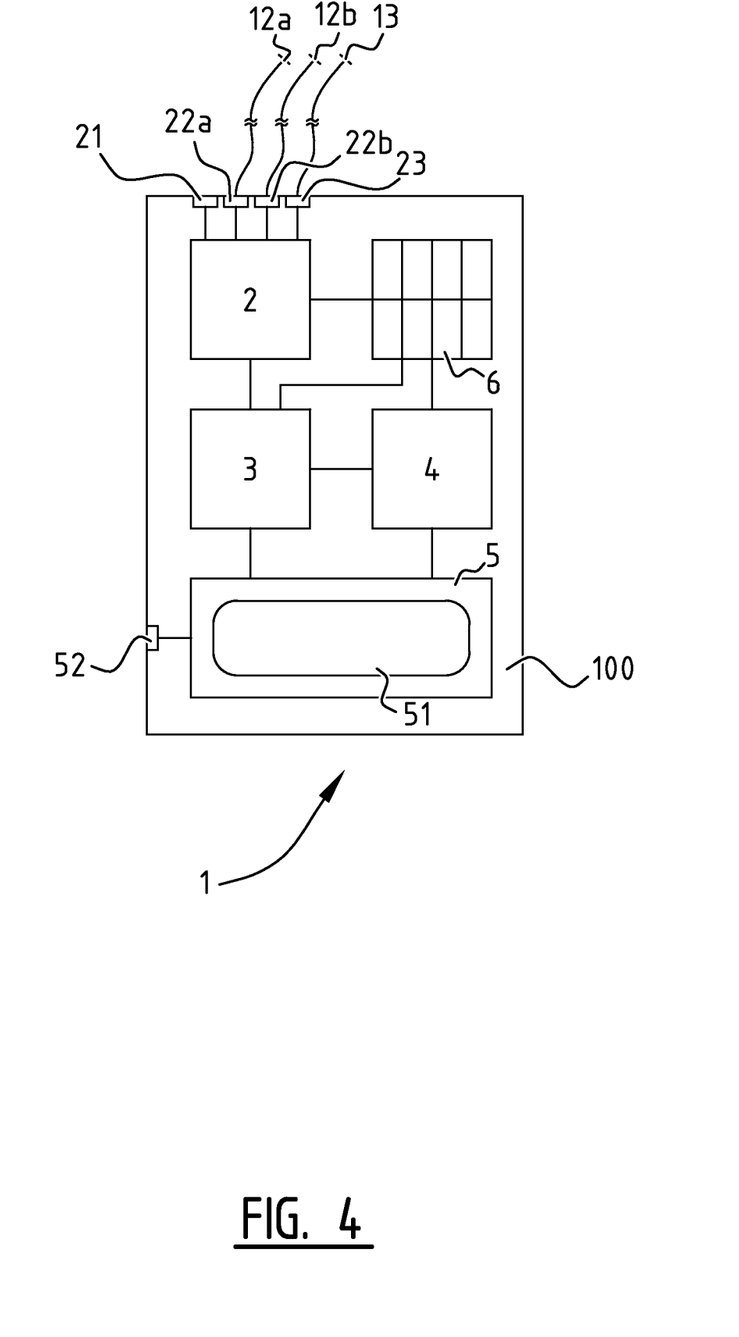
FIG. 4 schematically shows a device according to the invention.

With reference to FIG. 4, a device 1 is provided with a housing 100 which is provided with a memory 2 as input means for receiving EEG data. The EEG data can be obtained from connector 21 which can be used to connect the device 1 to any suitable data carrier. As an alternative, the EEG data may be recorded in real time. Thereto, the device 1 is provided with connectors 22a and 22b for connecting to electrodes 12a and 12b. A third connector 23 is provided for connecting a ground electrode 13. The electrodes 12a, 12b and 13 as such are arranged to be placed on the scalp of the patient.

Recording or transferring of the EEG data to the memory 2 can be initiated using suitable control means 6 in the form of a plurality of buttons. The control means 6 are operatively coupled to the memory 2. After transfer or after recording, the memory 2 contains EEG data comprising recording signals of the two electrodes 22a and 22b.

For processing the EEG data, a processor 3 is provided. After filtering the signals with a band pass filter having a lower threshold of 0.5 Hz and a higher threshold of 30 Hz, the bipolar deviation of the electrodes is obtained. The resulting signal is inputted to the analyzer 4, which is in this example shown as a separate part, although the analyzer 4 may be formed integrally with the processor 3. The signal as processed may also be stored, for instance in the memory 2.

The analyzer 3 calculates the relevant parameter which is indicative for a slowing of the signal as processed by the processor 3. Preferably, the relative power of the brain waves in the delta band is calculated. This relative delta power is then outputted to the output means 5 which comprise a screen 51 for outputting the parameter, for instance corrected to a predetermined scale of 0-10. The output means 5 are further provided with a connector 52 for connecting the device 1 to another processing unit such as a Personal Computer or a data carrier. It is further possible that the output means 5 comprise a memory, which may be shared with the input means 2, for storing the parameter.

Example for Determining Combinations of Locations and Parameter

EEGs according to the invention were recorded in 28 delirious patients and 28 age and sex-matched controls after cardiac surgery.

To study EEG characteristics we first focused on a uniform population of cardiothoracic surgery patients, who were admitted postoperatively to the ICU of the University Medical Centre Utrecht. The patients were recruited at the pre-operative outpatient clinic or at hospital admission prior to surgery. Patients were eligible for this study if they were 50 years or older and gave written informed consent. Exclusion criteria were a history of a neurological or psychiatric disease. Patients with a cerebrovascular event in medical history were not excluded, unless the event resulted in an EEG alteration. In that case the patient was excluded after the EEG recording. The Medical Ethics Committee of the University Medical Center Utrecht approved the study (protocol number 11-073).

Daily mental status screening was performed by research nurses and-physicians, with the Richmond Agitation and Sedation Scale (RASS) and the CAM-ICU during the first five post-operative days, or when surgery was complicated, the first five days that the patient was not in a comatose state. A comatose state was defined as a Glasgow Coma Score lower than 9 or a Richmond Agitation and Sedation Scale (RASS) score lower than minus 3. Delirium screening was conducted using the CAM-ICU. In addition, included patients were evaluated by a psychiatrist, geriatrician or neurologist, who made the final classification of mental status, based on the Diagnostic and Statistical Manual of mental disorders (DSM) IV criteria for delirium.

Thirty minute EEGs were recorded, in which non-delirious patients were asked to keep their eyes closed for 15 minutes of the recording. Because of the difficulty to instruct delirious patient, this group was not asked to close their eyes. To ensure that patients stayed awake, they were asked to conduct tasks like squeezing their hands at several time points during the recording. As a result of these tasks, the majority of delirious patients showed naturally an eyes closed period.

EEG recordings were conducted according to the international 10/20 system extended with an extra EOG electrode below the right eye. Recordings were performed with Micromed (Micromed, Trevisio, Italy), using a sample frequency of 512 Hz and G2 as ground electrode. Analog filter settings were set between 0.1 and 70 Hz. After digital storage the data was preprocessed using a band pass FIR filter with cut-off frequencies of 0.5 and 30 Hz. The signal processing toolbox EEGlab (Version 9.0.4.5s) was used for preprocessing of the EEG data in combination with MATLAB (Matlab, version 7.9.0.529, The MathWorks Inc, Natick, Mass. U.S.A).

For quantitative analysis, we selected the first 60 seconds of artifact free data with eyes closed. If specific electrode channels still contained artifacts, these channels were removed from the data. All electrode channels were used (F9, F10, Fp2, Fp1, F8, F4, Fz, F3, F7, T8, C4, Cz, C3, T7, P8, P4, Pz, P3, P7, O2, O1).

All EEG electrodes were combined with each other to create all possible bipolar EEG deviations. This resulted in 210 EEG deviations. EEG characteristics were determined including the relative power in the delta (rel_d, 0.5-4 Hz), theta (rel_t, 4-8 Hz), alpha (rel_a, 8-13 Hz) and beta (rel_b, 13-30 Hz) frequency band, the peak frequency and the slow-fast ratio (rel_d+rel_t/rel_a+rel_b). These 6 EEG characteristics were calculated per patient for every EEG deviation (see FIG. 1).

Patient characteristics were tested for normality using the Kolmogorov-Smirnov test. Normally distributed variables were presented using the mean and standard deviation (SD), non-normally distributed variables with the median and interquartile range (IQR). Statistical analysis of patient characteristics was conducted with Statistical Package for the Social Sciences (IBM SPSS Statistics, version 20, Armonk, N.Y., U.S.A.).

In explorative analysis all possible combinations of EEG deviations and characteristics were compared between delirious and non-delirious patients. It was assumed that not all EEG characteristics were normally distributed and therefore all comparisons were conducted using the Mann-Whitney U test. For registrations with eyes closed, all p-values were ranked and the smallest p-value was assumed to be the optimal EEG deviation and optimal EEG characteristic to distinguish delirious from non-delirious patients. For the 10 most optimal combinations of EEG characteristic and deviation, a receiver operating curve was created and the area under the curve was determined. The statistical analyses of the EEG data was performed with Matlab.

The 10 combinations of EEG deviation and EEG characteristic that showed the smallest p-value of all possible combinations in discriminating delirium from non-delirium for registrations with eyes closed are listed below:

| # | p | Dev | Par | D-median (IQR) | ND-median (IQR) | AUC | Sens (%) | Spec (%) |
|---|---|---|---|---|---|---|---|---|
| 1 | 1.8e−12 | F8-Pz | Rel. Delta | 0.59 (0.47-0.71) | 0.20 (0.17-0.26) | 0.99 | 100 | 96 |
| 2 | 3.7e−12 | F8-P3 | Rel. Delta | 0.59 (0.46-0.69) | 0.19 (0.15-0.26) | 0.99 | 96 | 96 |
| 3 | 1.1e−11 | F8-O2 | Rel. Delta | 0.60 (0.49-0.73) | 0.23 (0.18-0.30) | 0.99 | 96 | 96 |
| 4 | 1.5e−11 | Fp2-O1 | Rel. Delta | 0.66 (0.60-0.75) | 0.27 (0.23-0.36) | 0.99 | 96 | 95 |
| 5 | 1.7e−11 | F8-F4 | Rel. Delta | 0.60 (0.43-0.70) | 0.20 (0.17-0.26) | 0.98 | 96 | 92 |
| 6 | 2.2e−11 | F8-O1 | Rel. Delta | 0.62 (0.48-0.72) | 0.22 (0.17-0.26) | 0.99 | 96 | 95 |

| # | p | Dev | Par | D-median (IQR) | ND-median (IQR) | AUC | Sens (%) | Spec (%) |
|---|---|---|---|---|---|---|---|---|
| 7 | 2.4e−11 | F8-Cz | Rel. Delta | 0.57 (0.46-0.67) | 0.26 (0.20-0.33) | 0.98 | 91 | 96 |
| 8 | 2.4e−11 | F8-C3 | Rel. Delta | 0.57 (0.49-0.67) | 0.21 (0.17-0.30) | 0.98 | 91 | 92 |
| 9 | 2.9e−11 | Fp2-Pz | Rel. Delta | 0.64 (0.53-0.72) | 0.28 (0.22-0.36) | 0.99 | 100 | 95 |
| 10 | 3.0e−11 | Cz-O1 | Rel. Delta | 0.50 (0.37-0.57) | 0.17 (0.10-0.25) | 0.96 | 92 | 88 |

With:
: Rank,
p: p-value,
Dev: deviation,
Par: Parameter,
D-median: Delirium, median,
ND-median: non-Delirium median,
IQR: Inter Quartile Range,
AUC: Area Under the Curve;
Rel. Delta: Relative power in the delta frequency band,
Sens: Sensitivity,
Spec: Specificity.

The above table shows that the deviation F8-Pz for relative delta power showed the lowest p-value. Also neighboring electrodes of both F8 (for example Fp2) and Pz (for example P3) in combination with relative delta power showed very small p-values.

EXAMPLE 1

Measurement in 46 patients with eyes closed on locations F8-Pz with relative delta as indicative parameter. Comparison per patients the diagnosis according to the gold standard (DSM IV criteria) and indication (ind) according to EEG measurement based on threshold of 0.3757, With D: Delirium, ND: Non-Delirium:

| No. | DSM IV | Rel. Delta | Ind |
|---|---|---|---|
| 1 | D | 0.4058 | D |
| 2 | D | 0.5884 | D |
| 3 | D | 0.6411 | D |
| 4 | D | 0.5471 | D |
| 5 | D | 0.5503 | D |
| 6 | D | 0.4847 | D |
| 7 | D | 0.7052 | D |
| 8 | D | 0.7465 | D |
| 9 | D | 0.7416 | D |
| 10 | D | 0.7690 | D |
| 11 | D | 0.3757 | D |
| 12 | D | 0.6832 | D |
| 13 | D | 0.5834 | D |
| 14 | D | 0.6237 | D |
| 15 | D | 0.4654 | D |
| 16 | D | 0.5650 | D |
| 17 | D | 0.7209 | D |
| 18 | D | 0.3797 | D |
| 19 | D | 0.3769 | D |
| 20 | D | 0.7532 | D |
| 21 | D | 0.6995 | D |
| 22 | D | 0.4551 | D |
| 23 | ND | 0.3556 | ND |
| 24 | ND | 0.2819 | ND |
| 25 | ND | 0.3217 | ND |
| 26 | ND | 0.2168 | ND |
| 27 | ND | 0.3305 | ND |
| 28 | ND | 0.1573 | ND |
| 29 | ND | 0.1117 | ND |
| 30 | ND | 0.1691 | ND |
| 31 | ND | 0.2371 | ND |
| 32 | ND | 0.2234 | ND |
| 33 | ND | 0.3854 | D |
| 34 | ND | 0.0923 | ND |
| 35 | ND | 0.3702 | ND |
| 36 | ND | 0.2468 | ND |
| 37 | ND | 0.1887 | ND |
| 38 | ND | 0.1962 | ND |
| 39 | ND | 0.1383 | ND |
| 40 | ND | 0.1856 | ND |
| 41 | ND | 0.1806 | ND |
| 42 | ND | 0.1824 | ND |
| 43 | ND | 0.2423 | ND |
| 44 | ND | 0.1990 | ND |
| 45 | ND | 0.1606 | ND |
| 46 | ND | 0.2047 | ND |

EXAMPLE 2

Measurement in 47 patients with eyes closed on locations F8-P3 with relative delta as indicative parameter. Comparison per patients the diagnosis according to the gold standard (DSM IV criteria) and indication (ind) according to EEG measurement based on threshold of 0.3582, With D: Delirium, ND: Non-Delirium:

| No. | DSM IV | Rel. delta | Ind |
|---|---|---|---|
| 1 | D | 0.3771 | D |
| 2 | D | 0.5977 | D |
| 3 | D | 0.6004 | D |
| 4 | D | 0.6349 | D |
| 5 | D | 0.5011 | D |
| 6 | D | 0.5164 | D |
| 7 | D | 0.5006 | D |
| 8 | D | 0.7102 | D |
| 9 | D | 0.7601 | D |
| 10 | D | 0.6958 | D |
| 11 | D | 0.7819 | D |
| 12 | D | 0.3068 | ND |
| 13 | D | 0.6430 | D |
| 14 | D | 0.5460 | D |
| 15 | D | 0.5923 | D |
| 16 | D | 0.4467 | D |
| 17 | D | 0.5733 | D |
| 18 | D | 0.6836 | D |
| 19 | D | 0.3583 | D |
| 20 | D | 0.3582 | D |
| 21 | D | 0.6960 | D |
| 22 | D | 0.7031 | D |
| 23 | D | 0.4167 | D |
| 24 | ND | 0.3474 | ND |
| 25 | ND | 0.2034 | ND |
| 26 | ND | 0.3675 | D |
| 27 | ND | 0.2126 | ND |
| 28 | ND | 0.2704 | ND |
| 29 | ND | 0.1265 | ND |
| 30 | ND | 0.1368 | ND |
| 31 | ND | 0.1672 | ND |
| 32 | ND | 0.2563 | ND |
| 33 | ND | 0.1792 | ND |
| 34 | ND | 0.3433 | ND |
| 35 | ND | 0.0975 | ND |
| 36 | ND | 0.3158 | ND |
| 37 | ND | 0.2345 | ND |
| 38 | ND | 0.1459 | ND |
| 39 | ND | 0.1855 | ND |
| 40 | ND | 0.1234 | ND |
| 41 | ND | 0.1534 | ND |
| 42 | ND | 0.1354 | ND |
| 43 | ND | 0.1862 | ND |

-continued

| No. | DSM IV | Rel. delta | Ind |
|---|---|---|---|
| 44 | ND | 0.2156 | ND |
| 45 | ND | 0.2629 | ND |
| 46 | ND | 0.1671 | ND |
| 47 | ND | 0.1955 | ND |

EXAMPLE 3

Measurement in 46 patients with eyes closed on locations F8-02 with relative delta as indicative parameter. Comparison per patients the diagnosis according to the gold standard (DSM IV criteria) and indication (ind) according to EEG measurement based on threshold of 0.4399, With D: Delirium, ND: Non-Delirium:

| No. | DSM IV | Rel. delta | Ind |
|---|---|---|---|
| 1 | D | 0.4399 | D |
| 2 | D | 0.5924 | D |
| 3 | D | 0.7161 | D |
| 4 | D | 0.6960 | D |
| 5 | D | 0.5757 | D |
| 6 | D | 0.5970 | D |
| 7 | D | 0.4997 | D |
| 8 | D | 0.7555 | D |
| 9 | D | 0.7811 | D |
| 10 | D | 0.7274 | D |
| 11 | D | 0.8414 | D |
| 12 | D | 0.4897 | D |
| 13 | D | 0.7241 | D |
| 14 | D | 0.5679 | D |
| 15 | D | 0.6224 | D |
| 16 | D | 0.4528 | D |
| 17 | D | 0.5751 | D |
| 18 | D | 0.7533 | D |
| 19 | D | 0.4909 | D |
| 20 | D | 0.4638 | D |
| 21 | D | 0.7818 | D |
| 22 | D | 0.7232 | D |
| 23 | D | 0.3331 | ND |
| 24 | ND | 0.4751 | D |
| 25 | ND | 0.2961 | ND |
| 26 | ND | 0.4210 | ND |
| 27 | ND | 0.2338 | ND |
| 28 | ND | 0.3012 | ND |
| 29 | ND | 0.0925 | ND |
| 30 | ND | 0.0961 | ND |
| 31 | ND | 0.2014 | ND |
| 32 | ND | 0.2442 | ND |
| 33 | ND | 0.3027 | ND |
| 34 | ND | 0.3517 | ND |
| 35 | ND | 0.1052 | ND |
| 36 | ND | 0.3924 | ND |
| 37 | ND | 0.2568 | ND |
| 38 | ND | 0.2334 | ND |
| 39 | ND | 0.1838 | ND |
| 40 | ND | 0.1005 | ND |
| 41 | ND | 0.1341 | ND |
| 42 | ND | 0.1972 | ND |
| 43 | ND | 0.2676 | ND |
| 44 | ND | 0.1969 | ND |
| 45 | ND | 0.1983 | ND |
| 46 | ND | 0.1847 | ND |

The results can be summarized as follows:
Summary Table:

| Dev | Par | AUC | Sens (%) | Spec (%) | NPV (%) | PPV (%) |
|---|---|---|---|---|---|---|
| F8-Pz | Rel. delta | 0.99 | 100 | 96 | 100 | 96 |
| F8-P3 | Rel. delta | 0.99 | 96 | 96 | 96 | 96 |
| F8-O2 | Rel. delta | 0.99 | 96 | 96 | 96 | 96 |

With
Dev: Deviation,
Par: Parameter,
AUC: Area under the curve,
Sens: Sensitivity,
Spec: Specificity,
NPV: Negative Predictive Value,
PPV: Positive Predictive Value The method and system according to the invention therefore has a high prediction value, such that a reliable indication can be given whether a patient is delirious or not. The user is then able to judge whether a patient is delirious or not, taking this parameter into account, next to for instance other parameters or observations.

The present invention is not limited to the embodiment shown, but extends also to other embodiments falling within the scope of the appended claims.

What is claimed is:

1. A system for determining a parameter based on received electroencephalography (EEG) signals and determining whether a patient is delirious or not, or is at risk of becoming delirious based upon the determined parameter, wherein the system comprises:
   an input means for obtaining recording signals representative of brain activity from at least two electrodes but not all electrodes according to an extended 10-20 EEG system, wherein said at least two electrodes are configured to be located on different locations on a scalp of the patient;
   a processor arranged for determining a difference signal from a first recording signal from one electrode of said at least two electrodes and a second recording signal from another electrode of said at least two electrodes, wherein said at least two electrodes are selected from a group of electrode pairs located at or near locations selected from a group of electrode pair locations comprising F8-Pz, F8-P3, F8-O2, Fp2-O1, F8-F4, F8-O1, F8-Cz, F8-C3, Fp2-Pz, Cz-O1 according to the extended 10-20 EEG system:
   the processor being further arranged for:
   i) determining the parameter as a ratio of a spectral power of the difference signal in a delta band relative to a total spectrum power;
   ii) comparing the ratio with a threshold, wherein the threshold is dependent on the location of the selected pair of electrodes; and
   iii) outputting said parameter to an output.

2. The system according to claim 1, wherein the processor is further arranged for determining the ratio at different moments; and establishing a trend in the ratio.

3. The system according to claim 1, wherein the delta band has a frequency range of 0.5-4 Hz.

4. The system according to claim 1, wherein the total spectrum power of the difference signal is in a frequency range of 0.5-30 Hz.

5. The system according to claim 1, wherein the processor is further arranged for determining a statistical distribution for the ratio from the difference signal for at least one pair of electrodes corresponding to a delirium state and determining a statistical distribution for the ratio from the difference signal for at least one pair of electrodes corresponding to a non-delirium state.

6. The system according to claim 5, wherein the threshold for the electrode pair location at or near F8-Pz equals 0.3757.

7. The system according to claim 1, wherein said input means comprise an information carrier having stored thereon said recording signals representative of brain activity from at least two electrodes located on different locations on the patient's scalp.

8. The system according to claim 1, wherein said input means obtains signals from only two electrodes.

9. A method for determining a parameter based on received electroencephalography (EEG) signals and determining whether a patient is delirious or not, or is at risk of becoming delirious or not based upon the determined parameter, wherein the method comprises the steps of:
   at an input obtaining recording signals representative of brain activity from at least two electrodes but not all electrodes according to an extended 10-20 EEG system, wherein said at least two electrodes are located on different locations on a scalp of the patient;
   determining a difference signal from a first recording signal from one electrode of said at least two electrodes and a second recording signal from another one of said at least two electrodes, wherein said at least two electrodes are selected from a group of electrode pairs located at or near locations selected from a group of electrode pair locations comprising F8-Pz, F8-P3, F8-O2, Fp2-O1, F8-F4, F8-O1, F8-Cz, F8-C3, Fp2-Pz, Cz-O1 according to the extended 10-20 EEG system;
   a processor determining the parameter as a ratio of a spectral power of the difference signal in a delta band relative to a total spectrum power;
   said processor comparing the ratio with a threshold, wherein the threshold is dependent on the location of the pair of electrodes; and
   said processor outputting said parameter to an output.

10. The method according to claim 9, wherein the delta band has a frequency range of 0.5-4 Hz.

11. The method according to claim 9, wherein the total spectrum power of the difference signal is in a frequency range of 0.5-30 Hz.

12. The method according to claim 9, further comprising determining the ratio at different moments; and establishing a trend in the ratio.

13. The method according to claim 9, wherein the delta band has a frequency range of 0.5-4 Hz, and wherein the total spectrum power of the difference signal is in a frequency range of 0.5-30 Hz.

14. The method according to claim 9, further comprising said processor determining a statistical distribution for the ratio from the difference signal for at least one pair of electrodes corresponding to a delirium state and determining a statistical distribution for the ratio from the difference signal for at least one pair of electrodes corresponding to a non-delirium state.

15. The method according to claim 14, wherein the threshold for the electrode pair location at or near F8-Pz equals 0.3757.

16. The method according to claim 9, wherein said at an input obtaining recording signals representative of brain activity from at least two electrodes located on different locations on the patient's scalp comprises obtaining said recording signal from an information carrier.

17. The method according to claim 9, wherein said at an input obtaining recording signals representative of brain activity from at least two electrodes located on different locations on the patient's scalp comprises obtaining said recording signals from only two electrodes.

* * * * *